US011324864B2

(12) United States Patent
Guthrie et al.

(10) Patent No.: US 11,324,864 B2
(45) Date of Patent: May 10, 2022

(54) DISCRETE APPARATUS FOR THE EXPRESSION AND COLLECTION OF BREAST MILK

(71) Applicant: Moxxly LLC, Wilmington, DE (US)

(72) Inventors: Gabrielle V. Guthrie, San Francisco, CA (US); Santhi Analytis, San Francisco, CA (US); Cara C. Delzer, San Francisco, CA (US); Jacob Kurzrock, San Francisco, CA (US)

(73) Assignee: Moxxly, LLC, Wilmington, DE (US)

( * ) Notice: Subject to any disclaimer, the term of this patent is extended or adjusted under 35 U.S.C. 154(b) by 160 days.

(21) Appl. No.: 15/011,552

(22) Filed: Jan. 30, 2016

(65) Prior Publication Data
US 2016/0220745 A1 Aug. 4, 2016

Related U.S. Application Data

(60) Provisional application No. 62/109,773, filed on Jan. 30, 2015.

(51) Int. Cl.
*A61M 1/06* (2006.01)
(52) U.S. Cl.
CPC .............. *A61M 1/06* (2013.01); *A61M 1/066* (2014.02); *A61M 2205/3368* (2013.01)
(58) Field of Classification Search
CPC ............... A61M 1/066; A61M 1/0025; A61M 2205/3368; A61M 2205/3379; A61M 39/24; A61M 1/062; A61M 1/064; A61M 2205/07; A61M 2205/071; A61M 1/0072; A61M 1/0066; A61M 1/0644; A61M 1/068; A61M 2210/1007; A61M 2205/21; A61M 1/06–1/0697; A61M 2205/215;
(Continued)

(56) References Cited

U.S. PATENT DOCUMENTS 5,571,084 A * 11/1996 Palmer ................... A61M 1/06
601/14
6,440,100 B1 8/2002 Prentiss
(Continued)

OTHER PUBLICATIONS

Definition of interface, Dictionary.com, retrieved May 28, 2021, <https://www.dictionary.com/browse/interface> (Year: 2021).*
(Continued)

*Primary Examiner* — Brandy S Lee
*Assistant Examiner* — Hong-Van N Trinh
(74) *Attorney, Agent, or Firm* — Loyal Intellectual Property Law, PLLC; Travis Banta (57) ABSTRACT

Disclosed herein is a breast pump. The breast pump includes a milk capture system that includes a cupped flange. The cupped flange includes a nipple recess for receiving a nipple. The breast pump further includes a manifold which may be removably connected to the cupped flange. The manifold includes a nipple cavity in which vacuum suction is applied to a nipple. The manifold further includes a spout that drains milk away from the vacuum suction. The breast pump further includes a milk collection system which is removably connected to the manifold. The milk collection system includes a milk receptacle for containing milk expressed from a breast. Further disclosed is a breast pump system which includes a milk capture system, a manifold, and a milk collection system.

10 Claims, 6 Drawing Sheets

(58) Field of Classification Search
CPC ........ A61M 1/00–1/0023; A61J 1/1493; A61J 1/2089; A61J 1/2096
See application file for complete search history.

(56) References Cited

U.S. PATENT DOCUMENTS

| | | | | |
|---|---|---|---|---|
| 2005/0154349 | A1* | 7/2005 | Renz | A61M 1/06 604/74 |
| 2005/0228342 | A1* | 10/2005 | Yuen | A61M 1/06 604/74 |
| 2008/0000992 | A1* | 1/2008 | Mediare | G01K 11/12 235/494 |
| 2008/0275386 | A1* | 11/2008 | Myers | A61M 1/0068 604/74 |
| 2012/0041365 | A1* | 2/2012 | Simdon | A61M 1/06 604/74 |
| 2014/0288466 | A1 | 9/2014 | Alvarez et al. | |
| 2016/0082165 | A1* | 3/2016 | Alvarez | A61M 1/062 604/74 |

OTHER PUBLICATIONS

Definition of connect, Dictionary.com, retrieved May 28, 2021, <https://www.dictionary.com/browse/connect> (Year: 2021).*
Definition of envelop, Lexico, retrieved May 28, 2021, <https://www.lexico.com/en/definition/envelop> (Year: 2021).*
Jacqueline C. Kent et al., Importance of Vacuum in Breast Milk Expression; Breastfeeding Medicine, vol. 3, No. 1, Mar. 2008, pp. 11-19; New Rochelle, New York, USA.
Donna T. Ramsay et al., Milk Flow Rates Can Be Used to Identify and Investigate Milk Ejection in Women Expressing Breast Milk Using an Electric Breast Pump; Breastfeeding Medicine, vol. 1, No. 1, Mar. 2006, pp. 14-23, New Rochelle, New York, USA.

* cited by examiner

DISCRETE APPARATUS FOR THE EXPRESSION AND COLLECTION OF BREAST MILK

PRIOIORITY CLAIM

This application claims priority to U.S. Provisional Application No. 62/109,773, filed on Jan. 30, 2015, which is herein incorporated by reference in its entirety.

FEDERALLY-SPONSORED RESEARCH AND DEVELOPMENT

This invention was made without Government support. The Government has no rights in this invention.

FIELD OF THE INVENTION

This invention relates to breast pumps for nursing mothers.

OVERVIEW

Nursing women rely on a breast pump to express milk while away from their babies, yet current breast pumps are not well suited to today's user. Designed decades ago, the breast pump features obtrusive parts that require access to a private space to undress; considerable time and effort to assemble and clean many parts; and a disjointed storage system that often results in milk spills. Disclosed herein is a smart breast pump system that allows women to pump anywhere and get real-time information about their milk supply. Unlike existing flanges and bottles for pumping, the disclosed smart breast pump system is discrete and may be worn completely under regular clothing, without the need to disrobe or cover up with a blanket. The milk capture and collection system slides under the user's shirt or garment and is secured to the body by a standard nursing bra. The parts are simple to assemble and easy to wear. We augment the smart breast pump accessory parts (including flanges, bottles and pneumatic tubing) with sensors and an accompanying software application that runs on the user's smartphone or mobile device to help the user track information about her milk supply.

SUMMARY

Various aspects of the present disclosure are directed toward a smart breast pumping system that may be worn under the clothes. The system includes flanges, manifolds and milk receptacles, such as bottles or bags, which come in contact with human skin and/or bodily fluids.

More specific aspects of the present disclosure are directed to the context of a breast milk extraction apparatus that creates suction around the nipple of a lactating breast to extract and collect milk.

The capture (flange) and collection (bottle) systems fit under the user's clothes and are put on through the neck hole, or armhole, or under the bottom of the user's top. The flange is held to the body by any standard bra and cups the breast portion around the nipple. The bottle may hang under the bra or rest against the user's body. A manifold may be used to house the connection between the flange, the bottle and the pump mechanism. The pump mechanism may be attached directly to the capture portion of the device, with or without the use of pneumatic tubing.

The bottle easily connects and disconnects from the manifold and flange portion for pumping, cleaning and assembly. The discrete system may also include sensors for tracking milk flow rate and total volume pumped in real-time during milk expression.

Accordingly, disclosed herein is a breast pump. The breast pump includes a milk capture system that includes a cupped flange. The cupped flange includes a nipple recess for receiving a nipple. The breast pump further includes a manifold which may be removably connected to the cupped flange. The manifold includes a nipple cavity within which, vacuum suction is applied to a nipple by a pump. The manifold further includes a spout that drains milk away from the vacuum suction. The breast pump further includes a milk collection system which is removably connected to the manifold. The milk collection system includes a milk receptacle for containing milk drained into the milk receptacle through the spout in the manifold. Further disclosed is a breast pump system which includes a milk capture system, a manifold, and a milk collection system.

The above discussion/summary is not intended to describe each embodiment or every implementation of the present disclosure. The figures and detailed description that follow also exemplify various embodiments.

FIGURES

Various example embodiments may be more completely understood in consideration of the following detailed description in connection with the accompanying drawings.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DESCRIPTION OF EXAMPLE EMBODIMENTS

Various aspects of the present disclosure are directed towards apparatuses to benefit breastfeeding and breast pumping users. The primary user of the wearable system for milk extraction is the breastfeeding mother. Medical personnel may use the system for demonstrations and instructional purposes. Wearable sensors may measure data such as, but not limited to, flow rate, volume, and temperature of milk expressed by means of a breast pump.

The data collected by the sensor may be accessible via a software application to mothers and other caretakers including fathers, childcare providers, other family members, friends and medical personnel. While not necessarily so limited, aspects of the present disclosure are discussed in the exemplary context of apparatus (e.g., devices, tools and systems) and methods involving discreet body-worn methods to extract breast milk.

The major parts of the breast milk extraction system described include the capture system, collection system and manifold. The capture system is referred to as a flange, which covers the breast and surrounds the nipple for milk extraction. The collection system includes a bottle or bag which contains and stores collected milk. The collection system is connected in a removable manner to the manifold. The manifold further connects the capture system, including the flange, and the pump to the collection system. The manifold further includes a first pathway to create suction on the nipple while providing a separate second pathway for milk to fall into the bottle. The first pathway allows vacuum pressure provided by the pump to displace air and create suction around the nipple, yet the pathway is tortuous, preventing milk from moving into the suction pathway. In this way, milk falls away from vacuum suction and into the bottle. A sensor module may attach to one or more parts of the system and may include sensors, a radio module, a microprocessor, a battery and charging circuitry. In one embodiment, separate systems are provided for a left breast and a right breast and each individual system may include sensors, a radio module, a microprocessor, a battery, a pump, and charging circuitry.

The full apparatus is worn under the clothing for the extraction of breast milk and provides a number of advantages. First, the capture system comfortably conforms to the breast shape. The capture system further provides an airtight and liquid tight seal around the nipple and conveniently attaches to a milk collection system to prevent milk spills. The capture system further includes an actuator which causes milk extraction. Accordingly, the smart breast pump system may be persistently and discreetly worn under the clothes during milk extraction because it comfortably fits the contours of the body. The smart breast pump system may include a flexible neck portion between the capture system and the collection system to move the collection system away from or towards the user's body depending on their body shape for comfort, discretion, and to preserve proper function of the breast pump.

The capture system may fit comfortably and discreetly inside the user's bra. General dimensions for each capture cup (one size, S, M, L, XL, and etc.) may range between 3 and 5 inches in diameter, and may be less than 1 cm in thickness. The collection system may attach to the capture system. In different embodiments, the collection system may contain and store a total of 6 to 16 oz liquid volume. In one embodiment, the collection system may be leak proof. One or both of the collection system and the capture system may contain one or more sensor modules, each of which may occupy approximately one square inch of space and may be approximately one quarter of an inch thick.

The capture system includes a soft funnel like interior, and a bra cup shaped exterior portion. A rigid plastic section, or manifold, connects between the soft funnel like interior and the pneumatic tubing to the pump. Alternatively, the manifold may directly connect to a vacuum pump without tubing. In one embodiment, many portions of the capture system, such as the flange, may be made of flexible, soft, medical and/or food grade silicone or other flexible material. The capture system portions that come into contact with a body may be constructed from medical grade silicone. The capture system may be sanitized by dishwasher, microwave or boiling in hot water.

In one embodiment, many portions of the collection system may be made of flexible, soft, medical and or food grade silicone or other flexible material. Rigid plastic snaps allow the collection system to connect to the capture system and to external accessories such as feeding nipples. The connection between the capture and collection system may be leak proof. Furthermore, the collection system may be spill proof during disassembly and storage by utilizing a one-way valve that travels with it. The collection system may include a rigid portion to attach to the capture system. The smart breast pump system may have one or more planes of symmetry such that it may be stacked with other similar parts during storage. The collection system may also be sanitized by dishwasher, microwave or boiling in hot water.

The capture system and the collection system connect with minimal effort using snaps, quick connects or twist methods of attachment. In one embodiment, the sensors may turn ON when the various systems are connected to each other. A visual cue, such as a light, may alert the user that the system is ON and ready to measure and transmit data. The data may be viewed in real-time via the smartphone application.

The milk capture and collection system may include pneumatic tubing. The system may use an integrated pump or may use a remote pump.

Quick release connectors may connect the capture system to the pneumatic tubing and to the pump parts. The capture, collection and sensor components may fit inside a carrying case or bag. The carrying case or bag may include a section for charging the sensor module.

A flexible tube may connect the pump to the manifold for creating suction around the nipple. The pneumatic tubing may connect to a single or double electric breast pump. The pneumatic tubing may incorporate a diaphragm within a chamber, such that it creates a secondary vacuum pressure on the nipple, separate from the primary vacuum produced by the pump. This in turn produces a closed system, such that air around the nipple is not exposed to environmental air and air that passes through the pump parts. Furthermore, the closed system provides a barrier which prevents liquid from flowing back into the motor.

The smart breast pump system includes a method to vent air out of the milk collection system as milk is contained in the collection system. For example, air vents may be incorporated at the bottle top, and/or at a portion of the one-way valve between the capture and collection systems.

The pump within the smart breast pump system may be implemented using manual suction, centrifugal type vacuums, brushless motors, ultrasonic motors, and other types of pumps known in the art. The pump may also communicate with the sensor modules and a mobile device, such as a smart phone, to remotely or autonomously control its settings.

The sensor module may be an encased button, which snaps onto the manifold, or the capture and collection system. Since the sensor module is detachable from the manifold, capture, or collection system, the sensor module may be removed for charging and during cleaning. Sensors within the sensor module may use non-contact optical based methods for measuring flow rate and volume of the expressed milk, and body temperature and or milk temperature. The sensing methods may be mechanical, capacitive, ultrasonic, resistive or contact-based methods for measuring flow rate and volume of the expressed milk, body temperature and or milk temperature.

The embodiments and specific applications discussed herein may be implemented in connection with one or more of the above-described aspects, embodiments and implementations, as well as with those shown in the appended figures.

Figure 1:
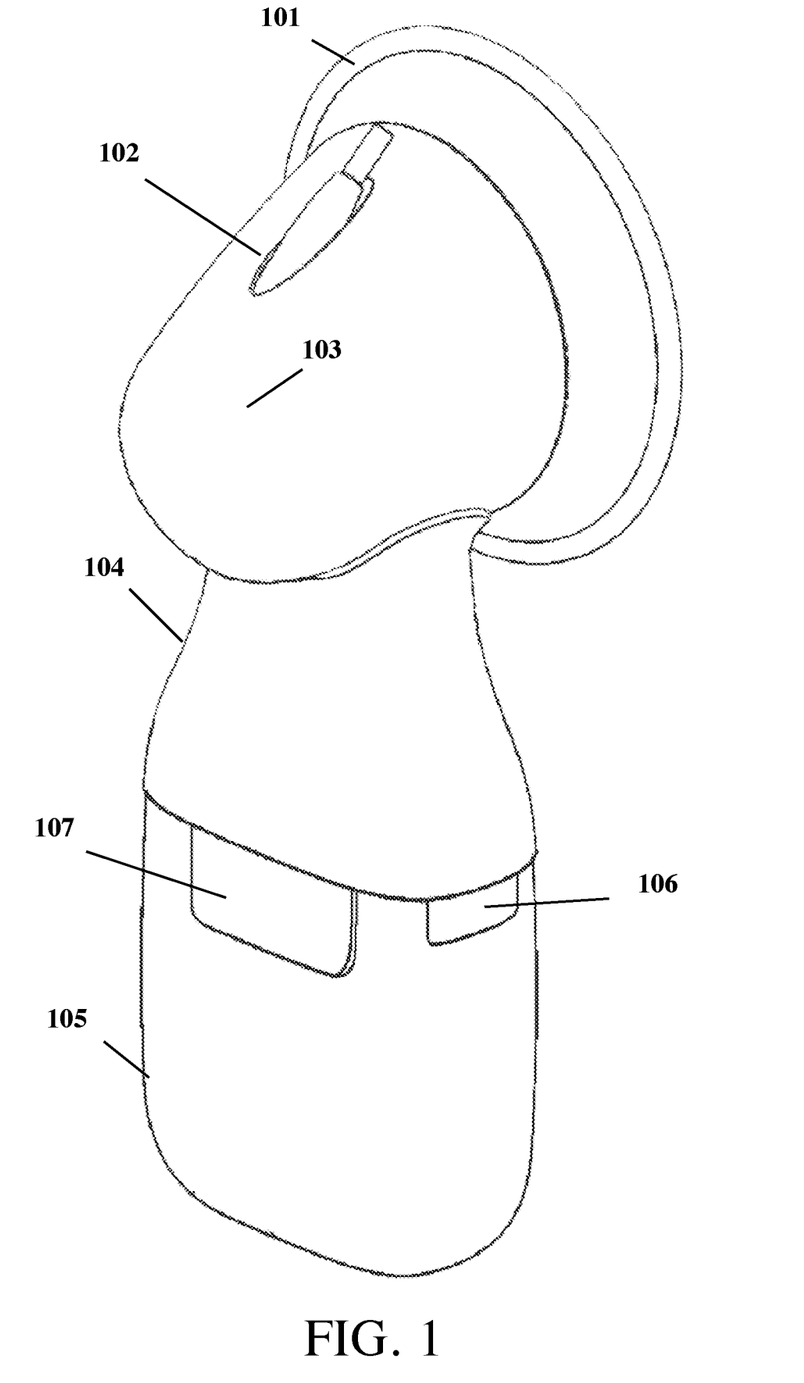
FIG. 1 shows an example embodiment of the smart breast pumping system, which may be worn on one breast.

Turning now to the figures, FIG. 1 shows an example embodiment of the smart breast pumping system, which may be worn on one breast. It is intended in most cases, however, that a user wear two of such systems to extract milk from both breasts simultaneously. Both systems may be symmetric or customized to the right and left breasts specifically. The flange 101 connects to manifold 104, which includes a flange connecting portion 102 that connects to or incorporates a pump to create suction on the nipple. The flange may be made of flexible, soft, medical and or food grade silicone or other flexible material. Upper manifold 103, which is included in manifold 104, cups the portion of the flange that surrounds the nipple, and milk falls through a spout within the manifold 104 and into the bottle 105. The bottle 105 has a flat profile allowing for ease of storage and the ability to be stacked. The manifold further connects to a rigid top portion of the bottle 105 by means of a snap mechanism and quick release button 106. Alternatively, the bottle may be released by squeezing the center or sides of the bottle and pulling it away from the manifold. A sensor module 107 may collect data from internal sensors such as a flow rate or volume of the expressed milk, and may be placed downstream from the milk flow at the bottom of the neck or top of the bottle. A sensor module may also be placed in upper manifold 103.

Figure 2A:
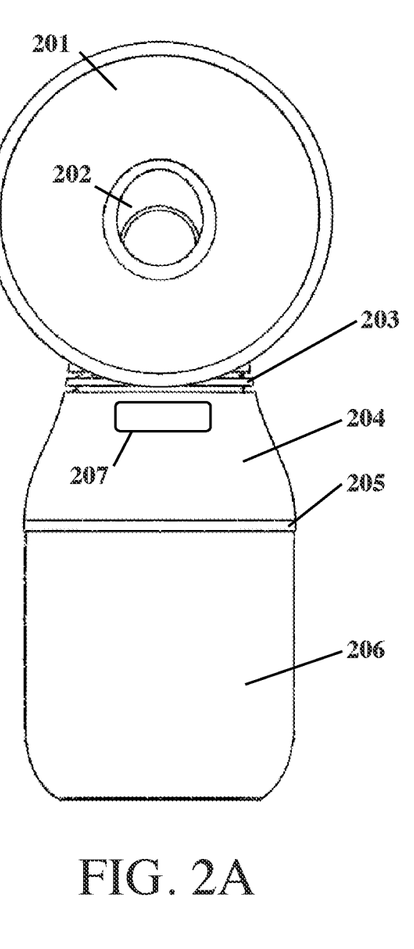
FIG. 2A shows the front view of an example embodiment of the smart breast pumping system, as seen from the user's perspective when worn.
Figure 2B:
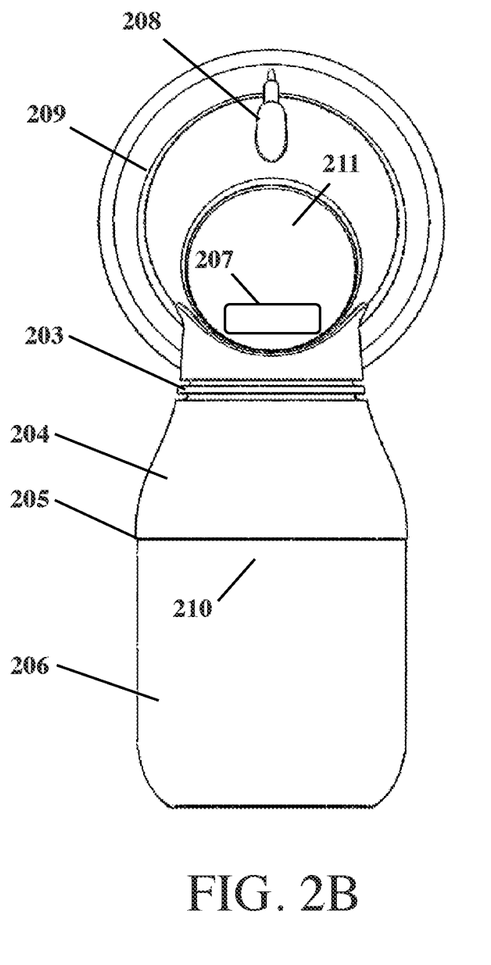
FIG. 2B shows the back view of an example embodiment of the smart breast pumping system, as seen when looking at the user when worn.

FIGS. 2A-2B show the front and back views of an example embodiment of the smart breast pump system. FIG. 2A shows a front view of the smart breast pump as it attaches to a user's breast. The flange 201 includes a nipple recess 202 that surrounds the user's nipple. A window 207 on the front of the manifold 204 as shown in FIG. 2A or the back of manifold 204 as shown in FIG. 2B may allow a sensor to track milk collection in real time. For example, a sensor may be placed on window 207 to track flow rate and volume of the expressed milk. As shown in FIGS. 2A and 2B, the neck portion of the manifold 204 may include a flexible portion 203, such as a bellow, to move the bottle 206 closer to or away from the user's body. The end of the manifold 204 may include a rigid portion to connect to a rigid collar portion 205 on the bottle. In FIG. 2B, an alternate sensor location 210 is on the bottle itself. The flange 201 portion may include a flexible lip in a ring shape 209 that folds over the edge of manifold 204 and is held in place by friction. The flange 201 connects to the manifold 204 by means of a detachable connection such as spring loaded quick release mechanisms, threaded or bayonet type twist attachments, or push-pull friction fittings. Other methods to connect the flange 201 to the manifold 204 for ease of reattachment include hook and eye, hook and loop, press-fit nodules, clips, and fasteners integrated into the flange and or manifold portions. The manifold may connect to a pump via an attachment portion 208 or have a pump motor integrated in the smart breast pump system at 211.

Figure 3:
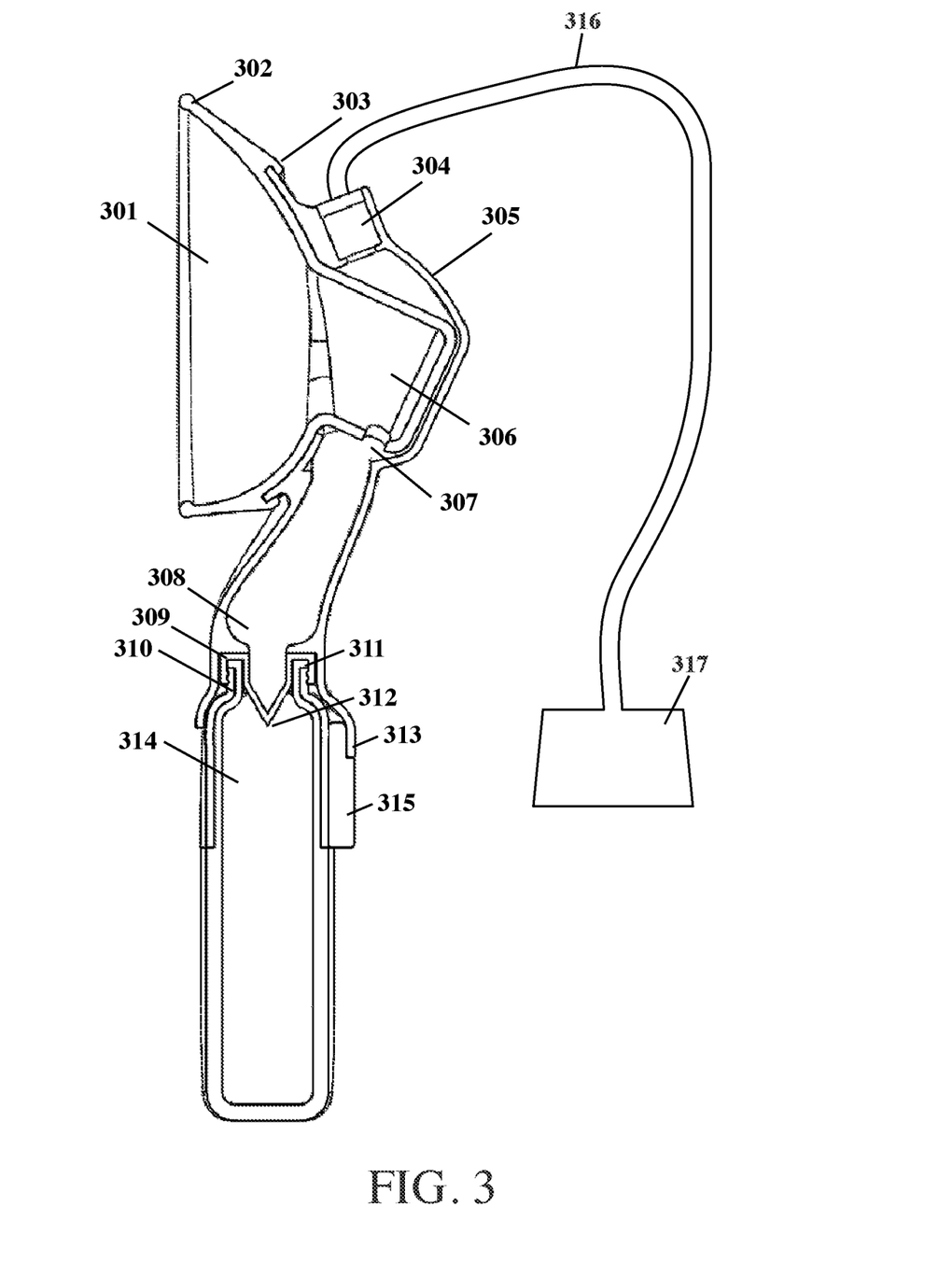
FIG. 3 shows a cross-sectional side view of an example embodiment of the smart breast pumping system, which may be worn on one breast.

FIG. 3 shows a cross-sectional side view of an exemplary embodiment of the smart breast pump system. The cut-away shows the flange 301, which includes a ribbed edge 302 to avoid tearing, a flexible lip 303 to attach to and detach from a top manifold portion 305, a portion that surrounds the nipple cavity 306, and a pathway for milk to fall into spout 307. The path of suction from the pump motor to the nipple area is tortuous for milk due to its curved and constrained features. Air is allowed to pass around the nipple area, however, milk is directed down and away from the pump. Accordingly, milk is prevented from being sucked into the pump. Connection at 303 may also be implemented using a rigid connection, or a rigid portion co-molded with a flexible portion.

The top manifold portion 305 includes a cavity 304 to interface with a mechanism to create suction around the nipple. This may include cavity 304 which houses a deformable gasket or circular ring and a tubular portion to mate with flexible pneumatic tubing 316 to connect to an electric pump motor 317. A mechanism to manually create suction may be attached at cavity 304 or in spout 307. A mechanism to electromechanically create suction may also be attached at cavity 304 or in spout 307. The pumping mechanism at cavity 304 may produce a force or pressure on the flexible flange 301 to cause compression and or massage on the user's breast.

As milk falls to the bottom manifold portion 308, it is held until a one-way valve 312 opens, causing milk to enter the bottle 314. The one-way valve 312 may comprise of one or multiple duckbill valves, valves with one or more pairs of leaflets, umbrella valves, ball check valves, or other type of check valves or one-way valves. The one-way valve 312 will open based on the release of pressure as the pump oscillates during the milk extraction process. The one-way valve 312 may include a portion outside of the seal between the capture and collection system that allows for air to vent out of the collection system into atmosphere, such that milk may fill and displace air in the collection system. The one-way valve 312 includes rim of the valve 309 that allows it to interface and connect to the rigid portion of the bottle collar 310 and or the manifold sensor connector 313. The rigid portion of the bottle collar 310 and or the rigid portion of the manifold sensor connector 313 may house the sensor module 315. The bottle may be fully rigid, or flexible with a rigid portion to aid in connections and prevent kinking. The flexible bottle may include a flexible lip 311, which interfaces between the rigid bottle collar 310 and the rim of the valve 309.

In practice, suction is applied by a pump 317 at cavity 304 to a user's nipple disposed within the nipple cavity 306 of flange 301. As milk is expressed through the user's nipple, gravity pulls milk down into spout 307 in the bottom manifold portion 308 despite the suction applied within nipple cavity 306. Milk remains in the bottom manifold portion 308 until one-way valve 312 opens and allows milk to fall into bottle collar 310. When disconnected, one-way valve 312 within the bottom manifold portion 308 remains attached to bottle collar 310 to prevent milk spills after a breast pumping session is completed.

Figure 4:
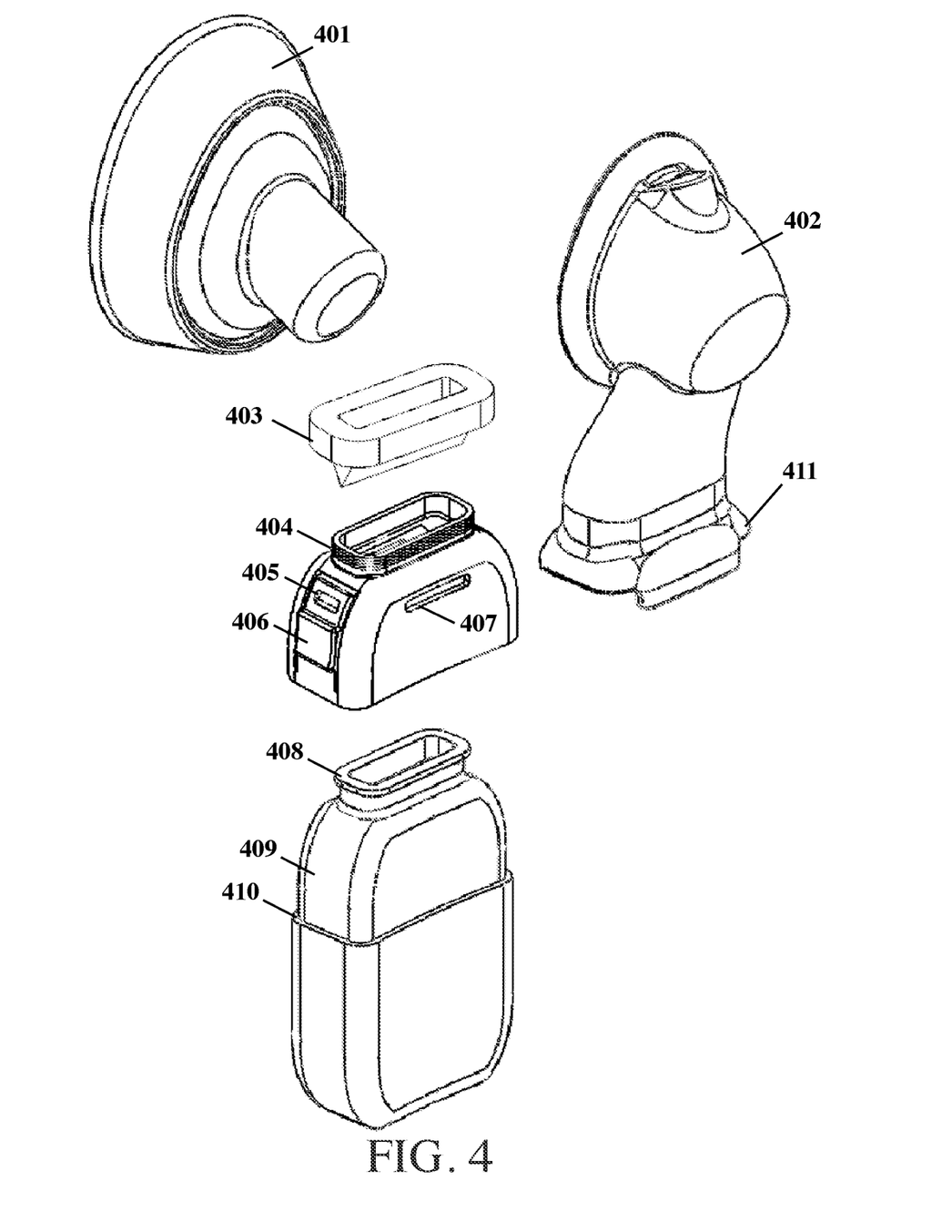
FIG. 4 shows an exploded assembly view of an example embodiment of the smart breast pumping system, which may be worn on one breast.

FIG. 4 shows an exploded assembly view of an example embodiment of the smart breast pump system, which includes the subparts that may be worn on one breast. The flange 401 connects to the manifold 402, which includes a portion 411 for attachment to the bottle collar. The bottle collar has a rim 404, which interfaces with a one-way valve 403, and a button 406 for quick release from the manifold. The quick release mechanism may be accomplished by a flexure with a slot 405 and mechanical button 406 on the bottle collar. The slot 405 interfaces with protruding features on the inside of the manifold in portion 411. The protruding features may be in the form of one or more pairs of tabs to click into grooves on the bottle or bottle collar. The bottle may consist of a single piece of flexible material consisting of a lip 408 and an indented portion 409 such that the rigid bottle collar will be flush to the main body of the bottle at the transition between bottle collar and shelf 410. The transition between bottle collar rim 404 and shelf 410 holds the bottle collar in place in concert with the bottle lip 408. The bottle collar may include a window 407 for the sensors to view milk as it is expressed. The bottle collar may be a rigid portion over molded, adhered or welded onto a flexible bottle such that it may have a rigid top portion and appear as one piece to the user. The bottle collar features may also be incorporated into the bottle itself as a single piece that is injection and/or blow molded in plastic. The bottle top may include the valve 403 when the bottle is disconnected from the manifold, making the bottle spill-proof as the user disassembles the apparatus. Accessories such as lids and feeding nipples may take the place of the one-way valve during storage, transportation, and baby feeding. A lid that covers the bottle may make use of the same features that the bottle uses to attach to the manifold, such as tabs and a groove to snap the lid onto the bottle. The portions of the flange, manifold and bottle may be sufficiently wide and or manipulable to allow for ease of cleaning of all parts.

Figure 5A:
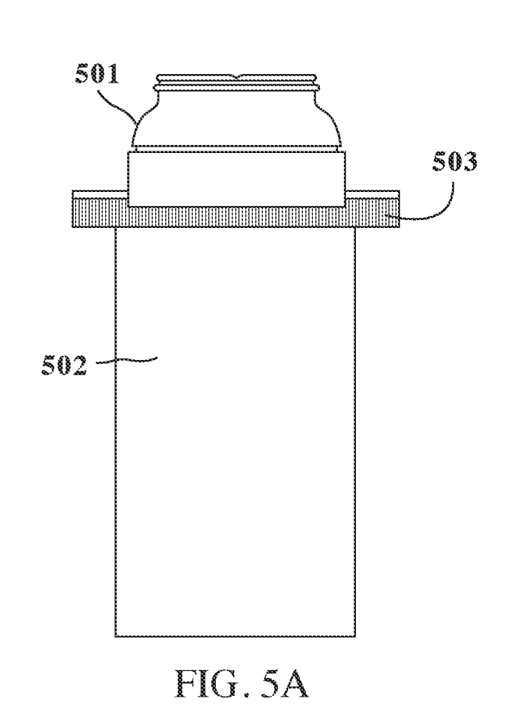
FIG. 5A shows an exemplary embodiment including a detachable milk storage bag for use during pumping.
Figure 5B:
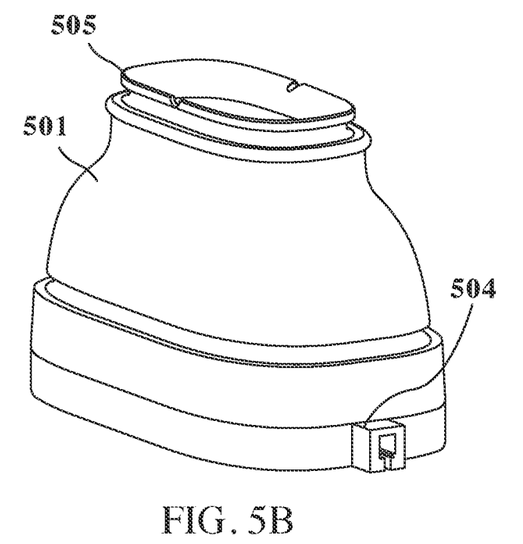
FIG. 5B shows another view of the exemplary embodiment including a detachable milk storage bag for use during pumping of FIG. 5A.
Figure 5C:
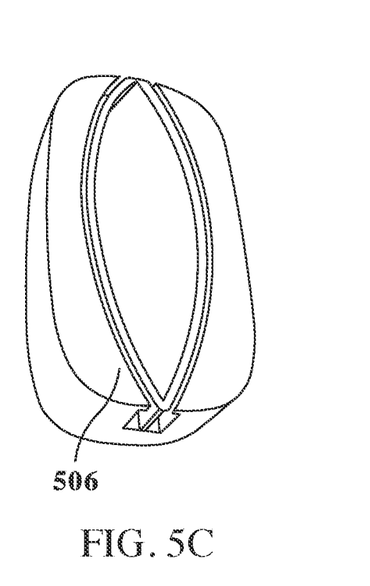
FIG. 5C shows another view of the exemplary embodiment including a detachable milk storage bag for use during pumping of FIG. 5A and FIG. 5B.

FIGS. 5A-5C illustrate an alternative embodiment of a milk collection vessel for use during pumping. In FIG. 5A, the milk collection vessel may be disposable and used for storing and transporting milk, and may be placed in a refrigerator or freezer. This vessel may be in the form of a bag 502 that is attached to an adapter 501, shown in FIG. 5B that either replaces the bottle collar shown in FIG. 4 or is part of the manifold neck portion. The bag 502 has an interlocking edge 503 that mates with itself to close the bag. The interlocking edge 503 is opened by a bag edge separator 504 that separates the interlocking edges 503 from each other into one of two curved tracks 506 on the underside of adapter 501, as shown in FIG. 5C. The base of the tracks allows for the interlocking edges 503 of the bag 502 to fit through, without releasing the bag through the underside of adapter 501. The tracks open the bag as it is installed in adapter 501, and close the bag on itself as it is pulled out of adapter 501. This self-locking mechanism will ensure that the bag is always closed while detached from the adapter 501. In this way, the bag may be resealable by reinterlocking the interlocking edges of the bag. The bag may also include graduation indicia printed on the side in order to easily see the volume of milk in the bag 502. A color coded dye may also be added on the outside of the bag that is either thermochromic to indicate when the milk is at room temperature, or to be included in a simple organization system. To reopen the bag 502 and allow for the transfer of fluids a spout that includes key to open the interlocking edges of the bag may be provided. Alternatively, the bag 502 may be torn along a perforation or cut with, for example, scissors. Adapter 501 may connect to one-way valve 312 as shown in FIG. 3 between the capture and collection systems, and feature a vent 505, shown in FIG. 5B, to allow air displaced by milk to escape the collection system. The vent 505 may be in the form of a notch or hole in the top of the bottle or in a portion of the manifold neck.

Figure 6A:
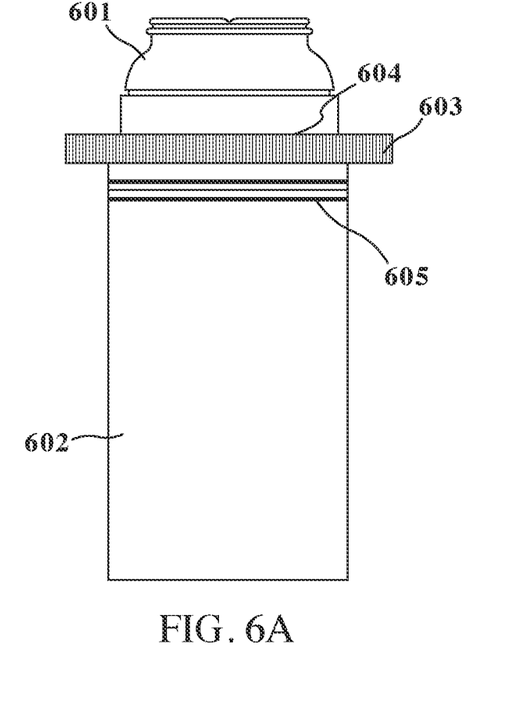
FIG. 6A shows an alternative example embodiment of a detachable milk storage bag system for use during pumping.
Figure 6B:
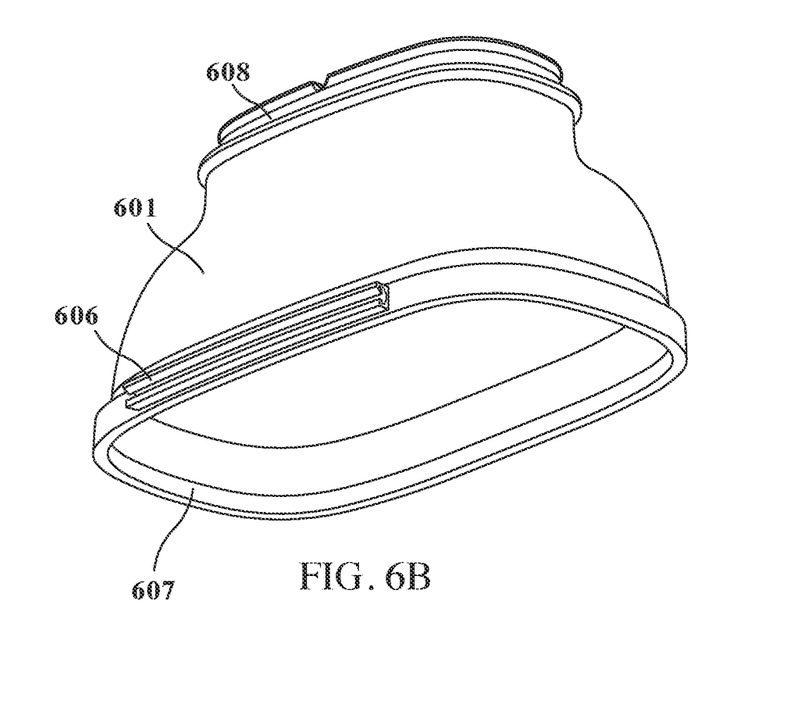
FIG. 6B shows another view of the exemplary embodiment of a detachable milk storage back system for use during pumping.

FIGS. 6A-6B illustrate another milk collecting vessel configuration and connection method. The adapter 601 holds the bag 602 by connecting to the top edge 603 of the bag 602. The adapter 601 includes a guiding element 604 that may snap or slide in to a guide rail 606 on the adapter to secure bag 602 to adapter 601. Preferably, once the bag 602 is attached to the guide rail 606, it may only be removed by sliding bag 602 back out of the guide rail 606. The adapter 601 may be a replacement to the bottle collar shown in FIG. 4, or incorporated into the collection system itself. A pair of continuous interlocks 605 are used to keep milk from spilling out of the bag during disassembly, transportation, and storage. The bottom 607 of adapter 601 may include connectors to connect with the collection system and features otherwise direct milk into the bag. The top 608 of the adapter 601 may include connectors to connect to the one-way valve between the capture and collection systems, and an air vent to allow air displaced by milk to escape the collection system.

What is claimed is:

1. A breast pump, comprising:
   a milk capture system, including a flange having a nipple recess disposed therein;
   a manifold including a top manifold portion and a bottom manifold portion, directly and removably connected to the flange, the top manifold portion including a nipple cavity in which vacuum suction is applied to a nipple, the top manifold portion further including: a spout draining milk in a direction that is away from the vacuum suction, and a sensor positioned in the bottom manifold portion;
   a milk collection system, removably connected to the manifold, including a milk receptacle for containing milk drained into the milk receptacle through the spout in the manifold, wherein the milk receptacle is positioned directly below a portion of the flange while the breast pump is in an upright position and the bottom manifold portion is positioned at an angle from a vertical plane extending vertically from the center of the milk receptacle; and
   a one-way valve interfacing with and connecting to a collar on the milk receptacle which defines an opening of the milk receptacle, the one-way valve enveloping the collar on the milk receptacle forming a spill-proof top for the milk receptacle when connected to the milk receptacle, the milk receptacle being insertable and connectable to the manifold during pumping to implement the one-way valve during pumping and as the spill-proof top which remains connected to the collar on the milk receptacle which defines the opening of the milk receptacle during removal from the manifold,
   wherein the one-way valve also interfaces with the manifold on an inside portion of the manifold to maintain a vacuum between the one-way valve and the manifold.

2. The breast pump of claim 1, wherein a remote pump is connected by pneumatic tubing to the manifold.

3. The breast pump of claim 1, wherein the one-way valve is disposed between the spout and the milk receptacle when inserted and connected to the manifold.

4. The breast pump of claim 3, wherein the one-way valve seals the milk receptacle when the milk receptacle is removed from the manifold.

5. The breast pump of claim 4, wherein the sensor positioned in the manifold tracks milk collection in real time.

6. The breast pump of claim 3, wherein the one-way valve comprises one or more duckbill valves.

7. The breast pump of claim 1, wherein the one-way valve includes a vent for the milk receptacle.

8. The breast pump of claim 1, wherein the bottom manifold portion provides a tortuous suction path from a pump motor to the nipple cavity.

9. The breast pump of claim 1, wherein the spout is disposed within the manifold and wherein the spout is connected to the nipple cavity.

10. The breast pump of claim 9, wherein the spout disposed within the manifold is connected to the nipple cavity by a hole in a surface that separates the nipple cavity from the one-way valve.

* * * * *